United States Patent [19]

Husain

[11] Patent Number: 4,708,850

[45] Date of Patent: Nov. 24, 1987

[54] SELF-CONTAINED PORTABLE APPARATUS FOR BLOOD TYPING

[76] Inventor: Abbas Husain, 5 W. Chestnut Ave., Merchantville, N.J. 08109

[21] Appl. No.: 735,616

[22] Filed: May 20, 1985

[51] Int. Cl.$^4$ .................. G01N 33/49; G01N 33/555; B01L 3/00
[52] U.S. Cl. ........................................ 422/61; 422/68; 422/73; 422/102; 422/104; 424/11; 436/520; 436/809
[58] Field of Search ...................... 422/61, 68, 73, 104, 422/102; 436/165, 520, 807, 809, 808; 424/11

[56] References Cited

U.S. PATENT DOCUMENTS

| Re. 29,725 | 8/1978 | Johnson et al. | 422/61 |
| 3,905,772 | 9/1975 | Harnett et al. | 23/259 |
| 4,076,592 | 2/1978 | Bradley | 435/33 |
| 4,162,003 | 7/1979 | Bartos et al. | 206/219 |
| 4,252,538 | 2/1981 | Barr | 23/230 |
| 4,275,053 | 6/1981 | Rosenfield et al. | 424/12 |
| 4,650,662 | 3/1987 | Goldfinger et al. | 422/102 |

FOREIGN PATENT DOCUMENTS

| 2921136 | 11/1980 | Fed. Rep. of Germany | 424/11 |
| 0066759 | 6/1981 | Japan | 422/61 |

OTHER PUBLICATIONS

E. A. Kabat et al., *Experimental Immunochemistry*, 2nd Edition, Charles C. Thomas, Springfield, Ill., 1961, p. 114.

Primary Examiner—Sidney Marantz
Assistant Examiner—David A. Saunders
Attorney, Agent, or Firm—William L. Muckelroy; Robert D. Thompson

[57] ABSTRACT

A plurality of ampules, individually formed, filled with reagents, sealed with a pane and marked with indicia for reagents to be mixed with blood in performing tests to determine blood type groups is disclosed. A receptacle for a blood sample which conveys the blood sample to the ampules and which accomodates a plurality of the ampules is also disclosed along with a means for rupturing each pane.

6 Claims, 8 Drawing Figures

SELF-CONTAINED PORTABLE APPARATUS FOR BLOOD TYPING

BACKGROUND OF THE INVENTION

1. Field of the Invention

This invention relates to an apparatus for use in performing tests to determine the blood type of a donor or patient according to the ABO classification system.

In our knowledge of blood physiology we know that the differences between the red blood cells of individuals lie in the chemical structures on the cell surfaces. These structures are called blood group antigens and are the result of inherited genes. We are also aware that the body produces antibodies which attack and destroy substances foreign to the host body. This is the underlying factor in the immunological reactions carried on in the human body. In fact the production of an antibody is stimulated by the introduction of the foreign substance. Foreign substances which stimulate the production of antibodies are termed antigens, and blood group antigens lead to the production of antibodies that will destroy the antigens and the red cells of which they are a part.

Inasmuch, as noted above, as the red blood cells of different individuals have different antigens, it is clear that in an emergent situation involving life or death from a trauma, on-site determination of blood type may be necessary for proper transfusion. If, in transfusing blood to a patient, the transfused donor's red blood cells had antigens different than those of the patient, the introduction of the donor's blood into the patient's blood stream would immediately stimulate the production of antibodies that would destroy the transfused blood and thereby vitiate the effects which it was desired to give the patient by the transfusion. It needs no emphasis to say that the consequences could be dire. On the other hand, if the red blood cells of the donor and the patient each had the same antigens, blood could be transfused from one to the other without any untoward incidents.

The foregoing is very well known, and it has led to a blood classification system based on the presence of the known blood group antigens. The principal blood group antigens are designated A and B, with some red cells having A antigens, some having B antigens, some having both A and B antigens, and some having neither antigen. These blood groups are designated, respectively, Type A, Type B, Type AB, and Type O. There are other genetic factors which have to be taken into account, but in general the foregoing blood group types offer a satisfactory preliminary categorization to help insure safe blood transfusions.

There is one other antigen that is significant and the presence or absence of which must be determined, and that is the Rh antigen. As are the other antigens referred to, it is an important factor in blood transfusions, but is especially important in pregnancy where an Rh negative mother who developed Rh antibodies during a previous pregnancy may transfer those antibodies to a fetus having Rh positive blood with possibly fatal results to the fetus or to the baby shortly after birth.

Blood cell compatibility is determined by the non-occurrence of an immunological reaction between antibodies contained in the blood serum of a patient and antigens present on blood cells from a donor. For example, if the red cells of patient are type A (i.e., have "A" antigens on the red cells), the serum of such a patient's blood will have anti-B antibodies, i.e., antibodies which will react with "B" blood, an immunological reaction will occur between the anti-B antibodies of the patient's serum and the B-antigens of the red blood cells of the donor. Such an incompatibility can result in intra-vascular hemolysis.

Test for blood cell typing and compatibility are generally of two types: (i) a test to determine whether a specific antibody added to the cells will cause their agglutination, and (ii) a test to determine whether a specific antibody added to the tested cells together with serum complement, will cause cell lysis.

The first of these two basic tests, agglutination, refers to a clumping of blood cells containing, for example, type A antigens, to which anti-A antibodies are added in the absence of complement. The A-antigen and the anti-A antibody react specifically with each other by immunological reaction with the antibody forming bridges between adjacent cells. This leads to an interlocked mass of the blood cells joined to each other by the added antibodies. This mass may be easily visually observed.

The second of the two tests referred to above, cell lysis, relates to the disruption of cell membranes leading to death of the cells and release of their intracellular contents. Cell lysis is the result of a reaction which occurs between cell membrane bound antibody and a group of potentially destructive proteins in normal serum (called "complement").

Both methods described above are used for the typing and compatibility testing of the cellular blood elements, erythrocytes, granulocytes, B and T lymphocytes, and platelets (thrombocytes). Both methods are intrinsically qualitative and each may be used separately for assay of antigen, antibody, and serum complement.

2. Description of the Prior Art

In blood cell typing and compatibility test procedures commonly used today, both agglutination tests and cell lysis tests are carried out in a liquid phase, that is, sera containing antibodies with or without complement to be tested are mixed with suspensions of the blood cells with respect to which blood typing or compatibility testing is to be evaluated. Normally, fixed volumes are employed.

Evaluation of agglutination test results requires the technician to distinguish agglutination of cells due to specific antigen-antibody molecular bridging from non-specific cell aggregation in which unrelated forces also cause some degree of clumping. The technician must also be able to distinguish free unagglutinated cells which may be present from clumped or agglutinated cells. This requires highly experienced personnel or precise particle sizing and counting with costly instruments. In addition, measurement of the degree of specific agglutination is either poorly semi-quantitative or is costly and complicated to perform.

While some instrumented tests for typing of red blood cells by agglutination have been developed, the equipment for these procedures is both costly and complicated to use. For example, one device which has been proposed for typing red blood cells by instrument is known as the "Auto Analyzer" of Berkman et al. described in Transfusion, Vol. 11, No. 6, pp. 317 et seq. (1971), and of Rosenfeld et al. described in Vox. Sang. 26:289-333, 1974. In the AutoAnalyzer, blood samples and antibody sera are combined under special circumstances in complex tubular coils designed to bring about agglutination. The sample from the reaction coils passes a "T" connection with the leg in a downward position so that agglutinates which are formed tend to be removed. Agglutination can be detected by measuring the decrease in optical density of the effluent from the "T" carrying the non-agglutinated fraction (Berkman et al. and Rosenfield et al.), or by trapping very strong agglutinates from the "T" on filter paper (Shield et al., Transfusion, Vol. 9, p. 348, 1969).

An alternative device is known as the "Groupmatic" and can cost several hundred thousand dollars (see Garretta et al., Vox Sang., Vol 27, p. 141, 1974). In the Groupmatic device, sera and blood cell suspensions are combined to produce agglutination. The presence of agglutination is detected by passing the suspension across two light beams, one of which passes through the center of the reaction cuvette while the other passes through the periphery. A difference in the transmission of the beams is taken as the measure of the strength of agglutination. Sophisticated circuitry is required, however, placing the instrument beyond use in the field by emergency personnel.

All liquid-phase hemagglutination tests, be they manual, "AutoAnalyzer", or "Groupmatic", suffer from a series of problems. Firstly, the manual tests lack the sensitivity of the instrumented tests so that clinically-significant red cell antigen-antibody reactions may be indiscernible by even the most experienced personnel. Secondly, unnecessary and unwanted protein in the reaction mixture may actually interfere with the development of hemagglutination, and cannot be removed readily without significant loss or elution of antibody. Thirdly, the red cells of about 2% of persons are unsuitable for sensitive evaluation by AutoAnalyzer (and presumably also by Groupmatic). Fourthly, red cells lose their sensitivity to specific hemagglutination on storage at 4° C., even for 2-3 weeks. Fifthly, not even the sensitive methods of Berkman et al. and Rosenfield et al. will detect all clinically-significant red cell antigen-antibody reactions. Lastly, "AutoAnalyzer" and "Groupmatic" tests are inefficient, lack portability, require stores of reagents, and are extremely tedious and can only be performed manually in a laboratory by the most experienced personnel.

These problems affect emergency blood typing where even routine red cell typing remains a time-consuming, manual operation that demands more skillful and experienced personnel than are available.

Hartnett, et al. in U.S. Pat. No. 3,905,772 describes an apparatus for performing blood typing tests which utilizes a plurality of test tubes formed as an integral unit together with a member that is marked vendorcators for reagents to be mixed in the tubes in performing the necessary tests to determine the blood type groups of various specimens. The apparatus is not portable and is not adapted for field use. Further, the apparatus is not self-contained and reagent and serum must be added to the blood samples and the test tubes.

In U.S. Pat. No. 4,275,053 issued June 23, 1981, Rosenfield, et al. describes a blood cell typing and compatibility procedure based upon either agglutination or immune lepis. A solid matrix is utilized and brought into contact with a serum containing the necessary antibodies for testing. Similarly, Barr in U.S. Pat. No. 4,252,538 issued Feb. 24, 1981, describes an apparatus and method for antibodies screening, typing and compatibility testing of red blood cells wherein a dual cavity substrate having a sample compartment for selectively discharging the blood specimen under test is rotably mounted in a holder. In the test procedure, a mono layer of red blood cells is centrifugally developed on the cavity surfaces of the substrate and subsequently typed.

Bartos, et al. in U.S. Pat. No. 4,162,033 describe a ready-for-use rapid test package for serological tests or in typing as carried out with preserved reactants in solid form in quantity suitably adjusted to each other. This invention utilizes reagents in ampules and makes possible an extraordinarily large number of serological investigations to a wide circle of users. The Bartos rapid test package makes possible screening of a large number of patients without the need to access large diagnostic laboratory facilities. The reactants in the ampules are preserved in frozen or freeze dried form for example Thus it is clear that the classification of a person's blood type must sometimes be done in an emergency yet the possibility of wrongful classification minimized, if not eliminated. This is especially true under out of the hospital situations involving disasters such as plane or train crashes where blood has to be transfused to a number of individuals sometimes after on the spot grouping.

In performing a blood grouping test, it is usual to test an individual's blood cells for the presence of antigens. Usually, a multiplicity of sample-containing test tubes must be used for the tests on an individual's blood. In a disaster area where numerous blood specimens must be typed simultaneously, the typing function involves many pipettings and agglutination observations that involve blood and reagents for each patient specimen. Such functions are not conductive to a field environment. Unless the utmost care is exercised at all times there is the danger that a test tube and contents associated with one individual will be interchanged with that of another or become contaminated. Even with the exercise of care, there is always the possibility of an inadvertent mix-up of test tubes, reagents, and contents being tested.

A major cost factor in making a determination of blood type according to the ABO classification system is the cost of a technican's time in mixing and distributing various reagents for individual blood grouping tests. Often times, errors result from the incorrect mixing of an inappropriate reagent with a blood sample.

OBJECTS OF THE INVENTION

It accordingly is an object of this invention to provide an improved blood group testing apparatus.

It is also an object of this invention to provide a blood group testing apparatus which is inexpensive to use.

It is another object of this invention to provide a blood group testing apparatus that minimizes the chance of interchanging individual blood samples undergoing testing.

It is still another object of the invention to provide a blood group testing apparatus that minimizes the possibility of introducing the wrong reagent to a sample being tested.

It is yet another object of the invention to provide a portable blood group testing apparatus that enables a technician to readily observe which reagent causes agglutination when that reaction occurs.

It is yet another object of the invention to provide a self-contained blood group testing apparatus that enables a technician to readily observe which reagent causes agglutination when the reaction occurs.

It is another object of the invention to reduce the time and tedium in performing blood grouping tests by eliminating the need to label and use a plurality test tubes and to reduce the number of items to be handled.

Features and advantages of the invention may be gained from the foregoing and from the description of a preferred embodiment of the invention which follows.

SUMMARY OF THE INVENTION

The present invention encompasses a method for determining the blood type of a small quantity of a blood specimen by causing portions of the blood sample to interact with pre-packaged ampules of blood anti-sera in a portable self-contained apparatus. An apparatus which is portable, self-contained with appropriate anti-sera capable of being easily and conveniently used in emergent conditions is also provided. The apparatus is made of a blood specimen receiving receptacle and at least three ampules, each with a sealed plenum and each having an open cavity therein for receiving a portion of a blood specimen prior to release of the anti-sera contained in each of the ampules.

DESCRIPTION OF THE PREFERRED EMBODIMENT

Figure 1:
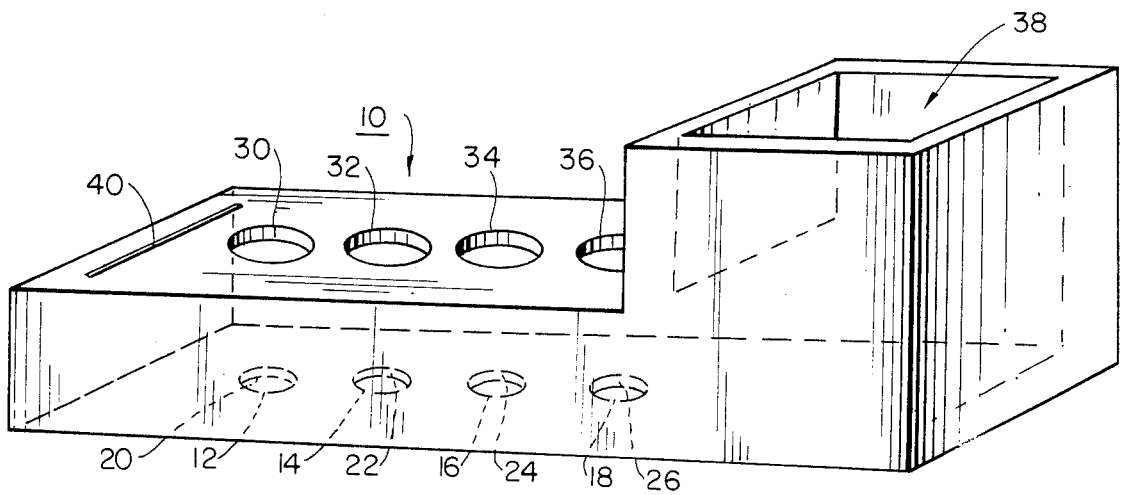
FIG. 1 is a perspective view showing a blood sample receptacle according to the novel invention.

Reference is to FIG. 1 of the drawing. There is shown a blood sample receptacle 10 according to the novel invention. The receptacle 10 is preferably molded as a single piece with a plurality of apertures, for example apertures 12, 14, 16 and 18. Each of the apertures 12, 14, 16 and 18 is adapted with threads 20, 22, 24 and 26, for example such that each aperture may be suitably closed.

The receptacle 10 is also adapted with a series of holes 30, 32, 34 and 36 located directly above the apertures 12, 14, 16 and 18, respectively. The holes 30, 32, 34 and 36 each have a diameter which is greater than a diameter of each of the respective apertures 12, 14, 16 and 18.

The receptacle 10 has a mouth 38 for receiving a blood sample such as drops of blood from a patient's finger, for example. The receptacle 10 also has at one end thereof, a marker 40. The marker 40 is prescribed at a location such that when a sufficient amount of a blood sample, for example 2 cc's, is received into the receptacle 10 to fill the receptacle 10 to the marker 40, there is basis for measurement of the sufficient amount of the blood sample to conduct blood typing tests by interacting portions of the blood sample with anti-A serum, anti-B serum and anti-Rh serum.

The receptacle 10 is made of translucent or clear plastic or glass, for example.

Figure 2:
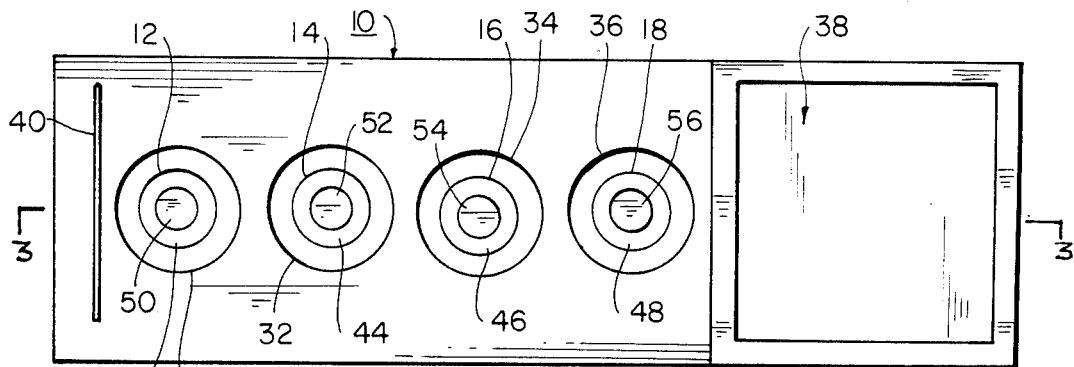
FIG. 2 is a top plan view of a blood sample receptable member and ampules according to the present invention.

Reference is now made to FIG. 2 of the drawing. There is shown a plan view of the receptacle 10 with a plurality of ampules 42, 44, 46 and 48. The ampules 42, 44, 46 and 48 are shown inserted into the apertures 12, 14, 16 and 18, respectively. The ampules 42, 44, 46 and 48 are observed through the holes 30, 32, 34 and 36 formed in the top of the receptacle 10. Inside each of the ampules 42, 44, 46 and 48 there are thin panes 50, 52, 54 and 56. These panes 50, 52, 54 and 56 are adapted to be either frangible, fracturable or rupturable. Accordingly, the panes 50, 52, 54 and 56 are made of foil, glass or plastic.

Figure 3:
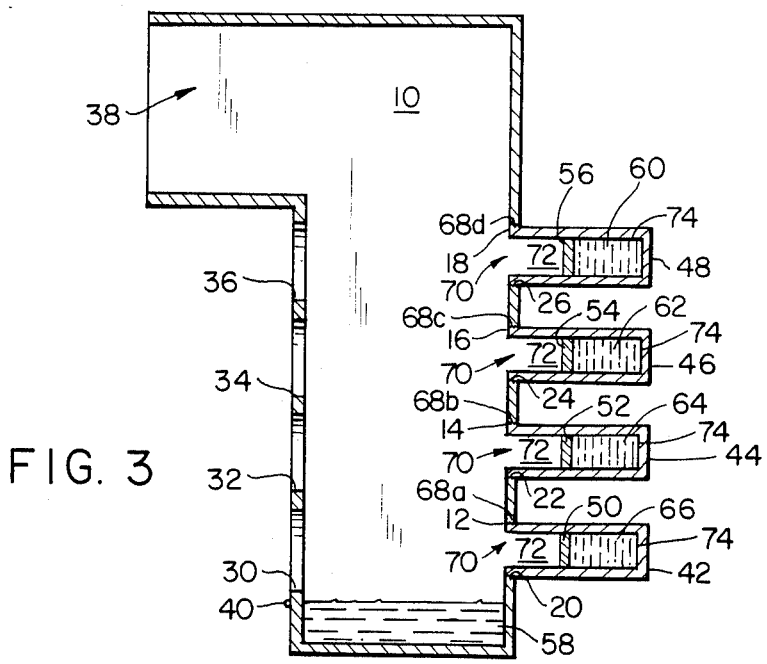
FIG. 3 is a sectional view of the novel invention taken along line 3—3 of FIG. 2.

Reference to FIG. 3 of the drawing. There is shown the receptacle 10 with each of the ampules 42, 44, 46 and 48 attached thereto. A blood specimen 58 is shown accumulated inside the receptacle 10 up to the marker 40. The ampule 48 is filled with a serum, anti-A serum 60, for example. The ampule 46 is also filled with a serum, anti-A serum 60, for example. The ampule 44 is likewise filled with a serum, anti-Rh serum 64, for example.

The blood sample receptacle 10, as shown in FIG. 1, has a fixed volumetric capacity, 10 cc, for example. A blood sample size of approximately 2 cc is suitable for properly performing blood grouping tests with the novel invention. The location at which the marker 40 is prescribed indicates that when a blood sample is collected and fills the receptacle 10 to the marker 40 with a blood specimen, for example specimen 58 as shown in FIG. 3, approximately 2 cc of blood has been collected from the patient's finger.

In the preferred embodiment of the invention, the receptacle 10 is coated with a substance which decreases the viscosity of the collected blood specimen 58 prior to collection of the specimen 58 in the receptacle 10.

The novel invention is adaptable to manufacture as an over the counter product for use by the general public. In the version of the novel invention offered to the general public for determination of blood type, the ampule 42 is filled with a blood viscosity decreasing substance 66, for example.

The ampules 42, 44, 46 and 48 are shown attached to the receptacle 10 by means of differently sized threads 68a, 68b, 68c and 68d which are formed around the outside of each of the ampules 42, 44, 46 and 48 near an orifice 70 formed in each of the ampules 42, 44, 46 and 48. Each of the ampules 42, 44, 46 and 48 also has a cavity 72 which is accessed through the orifice 70. Each of the cavities 72 is adjacent a plenum 74 in each of the ampules 42, 44, 46 and 48. The plenum 74 of the ampule 48 is filled with the anti-A serum 60. The plenum 74 of the ampule 46 is filled with the anti-B serum 62. The plenum 74 of the ampule 44 is filled with the anti-Rh serum 64. The plenum 74 of the ampule 42 is filled with the substance 66. The cavities 72 are separated from the plena 74 for each of the ampules 42, 44, 46 and 48 by the panes, 50, 52, 54 and 56, respectively. Each plenum 74 may be separately constructed entirely of either foil, glass or plastic and inserted in close fit fashion into an ampule.

The threads 68a, 68b, 68c and 68d are adapted to mate respectively with the threads 20, 22, 24 and 26 formed in the respective apertures 12, 14, 16 and 18.

The threads 20, 22, 24 and 26 are each distinctively sized such that the ampule 42, with its thread 68a, is specifically adapted to be inserted and fit only the threads 20 in the aperture 12. Likewise, the ampule 44 can only be fitted into the aperture 14. The ampule 46 can only be fitted into the aperture 16. The ampule 48 can only be fitted into the aperture 18. This arrangement is a feature of the novel invention such that the possibility of error by a technician misreading a reaction in either one of the ampules is substantially reduced. This arrangement is in addition to a specific label (See FIG. 8) placed on each of the ampules to denote the contents thereof. Thus, a reaction in the ampule located in the aperture 14 is known to be a reaction with the anti-Rh serum 64 and therefore denotes an Rh positive blood sample. A reaction in the ampule 46 located in the aperture 16 which contains anti-B serum 62 is noted to be a reaction with a blood specimen which is type B. A reaction in the ampule 48 in the aperture 18 which contains anti-A serum 60 is noted to be with a blood sample which is type A. A reaction with the blood sample 58 in both the ampules 46 and 48 denotes blood type AB. The absence of the observation of a reaction in both ampule 48 and ampule 46 denotes the blood type O.

Figure 4:
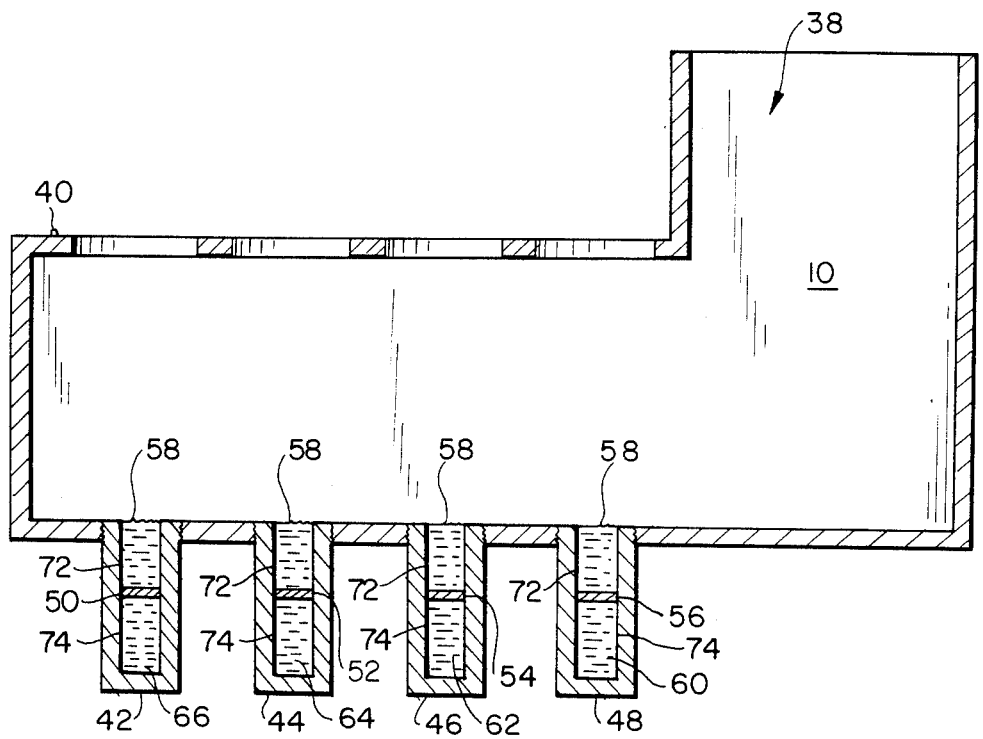
FIG. 4 is a sectional view of a blood sample receptacle and ampules of the novel invention.

Attention is now directed to FIGS. 3 and 4. In the method of the invention the blood sample 58 is distributed among the cavities 72 through the orifices 70 in each of the ampules 42, 44, 46 and 48 by rotating the receptacle 10 shown in FIG. 3 ninety degrees clockwise. The blood sample redistributes among the cavities 72 such as shown in FIG. 4, for example. The blood sample 58 is shown distributed and filling cavities 72 in each of the ampules 42, 44, 46 and 48. The blood sample 58 is separated from the contents of each ampule by the panes 50, 52, 54 and 56. A portion of the blood sample 58 is located above the pane 50. Another portion of the blood sample 58 is located above the pane 54. Similarly, there is a portion of the blood sample 58 located above the pane 56. Thus, a step in the method of the novel invention is to place a portion of the blood sample 58 adjacent a plenum 74 inside each of the ampules 42, 44, 46 and 48.

In FIG. 4 there is shown a plurality of openable panes 50, 52, 54 and 56 in each of the ampules 42, 44, 46 and 48, respectively. These panes are made of glass, foil or a thin plastic material which seals or blocks off a closed end of each of the ampules 42, 44, 46 and 48 so as to form a closed plenum for containment of a liquid such as an anti-serum, anti-coagulent or blood dilutant.

Figure 5:
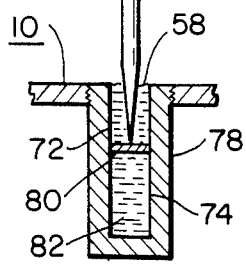
FIG. 5 is a fragmentary sectional view of an ampule and member of the novel invention; and, FIG. 6 is a fragementary sectional view of an ampule of the novel invention with its plenum fractured.

Reference is now made to FIG. 5 wherein there is shown a fragmented view of a typical ampule 78 similar for example to either ampule 42, 44, 46 or 48. Shown there is a blood sample, e.g., the blood sample 58, in a cavity, for example cavity 72. The blood sample 58 is in the cavity 72 separated from a plenum, for example plenum 74. Adjacent the cavity 72 is a pane 80 similar to the panes 50, 52, 54 and 56. The liquid 82 occupying the plenum 74 may be selected to be either of the anti-sera 60, 62 or 64 or the substance 66 as more fully shown in FIG. 4.

There is shown poised above the pane 80 a means 84 for opening the pane 80. The means 84 is an elongated pin, for example made of glass, metal, plastic or the like. The means 84 is sufficiently rigid such that when pushed downward against the pane 80, the pane 80 is caused to fracture or sufficiently puncture according to the material selected for the pane 80.

The pane 80 may be made of a flexible plastic material which is non-frangible and yet puncturable. However, in one preferred embodiment of the novel invention, the pane 80 is made of glass and fracturable.

Figures 6, 7:
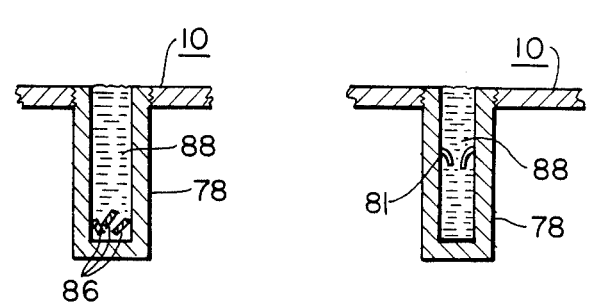
FIG. 7 is a fragmentary sectional view of an ampule of the novel invention with its plenum ruptured.

Attention is now directed to FIG. 6 wherein the pane 80 is shown fractured into several pieces 86. The liquid 82 mixes with the blood sample 58 to form a mixture 88 in the ampule 78 as the pieces 86 are produced.

Referring now to FIG. 7, a pane 81 is illustrated as pliable yet puncturable. The pane 81 is shown ruptured by the means 84. Subsequent to the rupture of the pane 80 by the means 84, the means 84 is used to mix or stir the blood specimen 58 with the contents 82 in the ampule to form the mixture 88 and to effectuate complete mixing.

Figure 8:
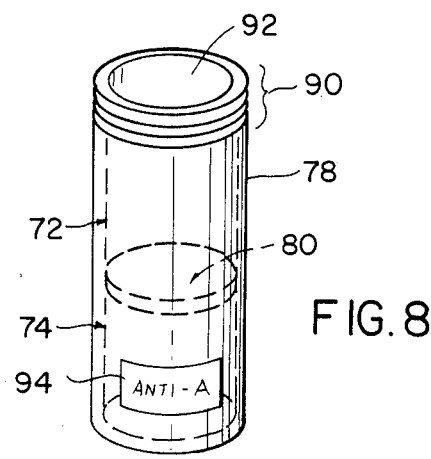
FIG. 8 is a sectional view of an ampule of the novel invention.

There is shown in FIG. 8 a perspective view of an ampule, for example the ampule 78. There is shown a cavity, for example cavity 72, separated by a pane 80 from a plenum, e.g., plenum 74 within the ampule 78. The ampule 78 is shown with threads 90 arranged about an orifice 92.

There is also illustrated a label 94 for the ampule 78 bearing the designation "Anti-A" for example to denote the contents of the plenum 74, for example.

Having thus described the novel invention, it is clear that what may appear to be different embodiments thereof, may be produced and provided without departing from the spirit, intent and scope of the invention as described by the specification. Hence, it is intended that the foregoing specification and the drawing be interpreted as illustrative rather than limiting the foregoing claims which are to be applied and interpreted pursuant to the doctrine of equivalents, to wit:

What is claimed is:

1. In a testing apparatus for determining the blood group of a patient's blood sample, the combination of a receptacle member, a plurality of separately sealed ampulses each containing a distinct anti-serum, said ampules each being detachably joined to a distinct, and non-interchangeable separate site on the receptacle member, the receptacle member having a single chamber with an aperture through which the blood sample is admitted, each said ampule having a plenum sealed by a pane having two faces, one of said faces being exposed to the anti-serum in said ampule and the other said face being exposed to the blood sample, and a separate means for opening each said plenum.

2. The testing apparatus of claim 1 wherein one of said ampules contains anti-A serum, a second one of said ampules contains anti-B serum and a third said ampule contains anti-Rh serum.

3. The testing apparatus of claim 2 wherein the plenum of each of three said ampules is filled with an anti-serum and wherein each said ampule has an open cavity adapted to receive a portion of said blood sample and wherein each said cavity is located adjacent said anti-serum in said ampule, a bottom for said cavity being formed by said pane.

4. The testing apparatus of claim 3 further comprising a like plurality of individual means for opening each pane of each ampule.

5. The testing apparatus of claim 4 further comprising a fourth ampule containing a substance, said ampule being connected to said receptacle member at a distinct, non-interchangeable site.

6. The testing apparatus of claim 5 wherein said substance comprises a blood thinner.

* * * * *